US010632218B2

(12) United States Patent
Lepez et al.

(10) Patent No.: US 10,632,218 B2
(45) Date of Patent: Apr. 28, 2020

(54) METHOD AND DEVICE FOR THE CONTINUOUS OZONE-BASED TREATMENT OF PARTICULATE PRODUCTS, COMPRISING MEANS FOR CONVEYING AND VIBRATING SAID PRODUCTS

(71) Applicant: E.T.I.A.—EVALUATION TECHNOLOGIQUE, INGENIERIE ET APPLICATIONS, Compiegne (FR)

(72) Inventors: Olivier Lepez, Lamorlaye (FR); Philippe Sajet, Lacroix Saint-Ouen (FR); Tatiana Guzun, Compiegne (FR)

(73) Assignee: E.T.I.A.—EVALUATION TECHNOLOGIQUE, INGENIERIE ET APPLICATIONS, Compiegne (FR)

( * ) Notice: Subject to any disclaimer, the term of this patent is extended or adjusted under 35 U.S.C. 154(b) by 18 days.

(21) Appl. No.: 15/560,851

(22) PCT Filed: Apr. 8, 2016

(86) PCT No.: PCT/EP2016/057812
§ 371 (c)(1),
(2) Date: Sep. 22, 2017

(87) PCT Pub. No.: WO2016/162511
PCT Pub. Date: Oct. 13, 2016

(65) Prior Publication Data
US 2018/0117199 A1 May 3, 2018

(30) Foreign Application Priority Data
Apr. 10, 2015 (FR) ...................................... 15 53146

(51) Int. Cl.
*A61L 2/20* (2006.01)
*A61L 2/18* (2006.01)
(Continued)

(52) U.S. Cl.
CPC .............. *A61L 2/202* (2013.01); *A23B 7/152* (2013.01); *A23C 3/005* (2013.01); *A23L 3/3409* (2013.01);
(Continued)

(58) Field of Classification Search
CPC ......................................................... A61L 2/202
See application file for complete search history.

(56) References Cited

U.S. PATENT DOCUMENTS 3,687,264 A * 8/1972 Jackson ................. A47L 21/02
198/373
4,771,894 A * 9/1988 Lapp ...................... B03B 9/061
198/770

(Continued)

FOREIGN PATENT DOCUMENTS

| GB | 2517022 A | 2/2016 |
|---|---|---|
| WO | WO 2009/019570 A2 | 2/2009 |
| WO | WO 2009-019570 A3 | 6/2009 |

*Primary Examiner* — Donald R Spamer
(74) *Attorney, Agent, or Firm* — Muncy, Geissler, Olds & Lowe, P.C.

(57) ABSTRACT

A method of treating a substance in the form of divided solids, includes the steps of introducing the substance into an enclosure in which there exists an ozonated atmosphere under pressure, conveying the substance in the enclosure with a continuous movement in such a manner that the substance is located continuously in the ozonated atmosphere while it is being conveyed in the enclosure, the substance being conveyed by vibration means causing the enclosure to vibrate, and unloading the substance from the enclosure via the outlet after a single passage of the substance through the enclosure.

10 Claims, 1 Drawing Sheet

(51) Int. Cl.
   *A23L 3/3409* (2006.01)
   *A23B 7/152* (2006.01)
   *A23C 3/00* (2006.01)
   *A23L 3/3445* (2006.01)
   *A61L 2/26* (2006.01)

(52) U.S. Cl.
   CPC ............ *A23L 3/3445* (2013.01); *A61L 2/183* (2013.01); *A61L 2/26* (2013.01); *A23V 2002/00* (2013.01); *A61L 2202/122* (2013.01); *A61L 2202/15* (2013.01); *A61L 2202/21* (2013.01)

(56) References Cited

U.S. PATENT DOCUMENTS

| | | | | |
|---|---|---|---|---|
| 5,376,265 A | * | 12/1994 | Szabo | A61L 2/202 210/120 |
| 2007/0172384 A1 | * | 7/2007 | Liang | A61L 2/04 422/38 |

* cited by examiner

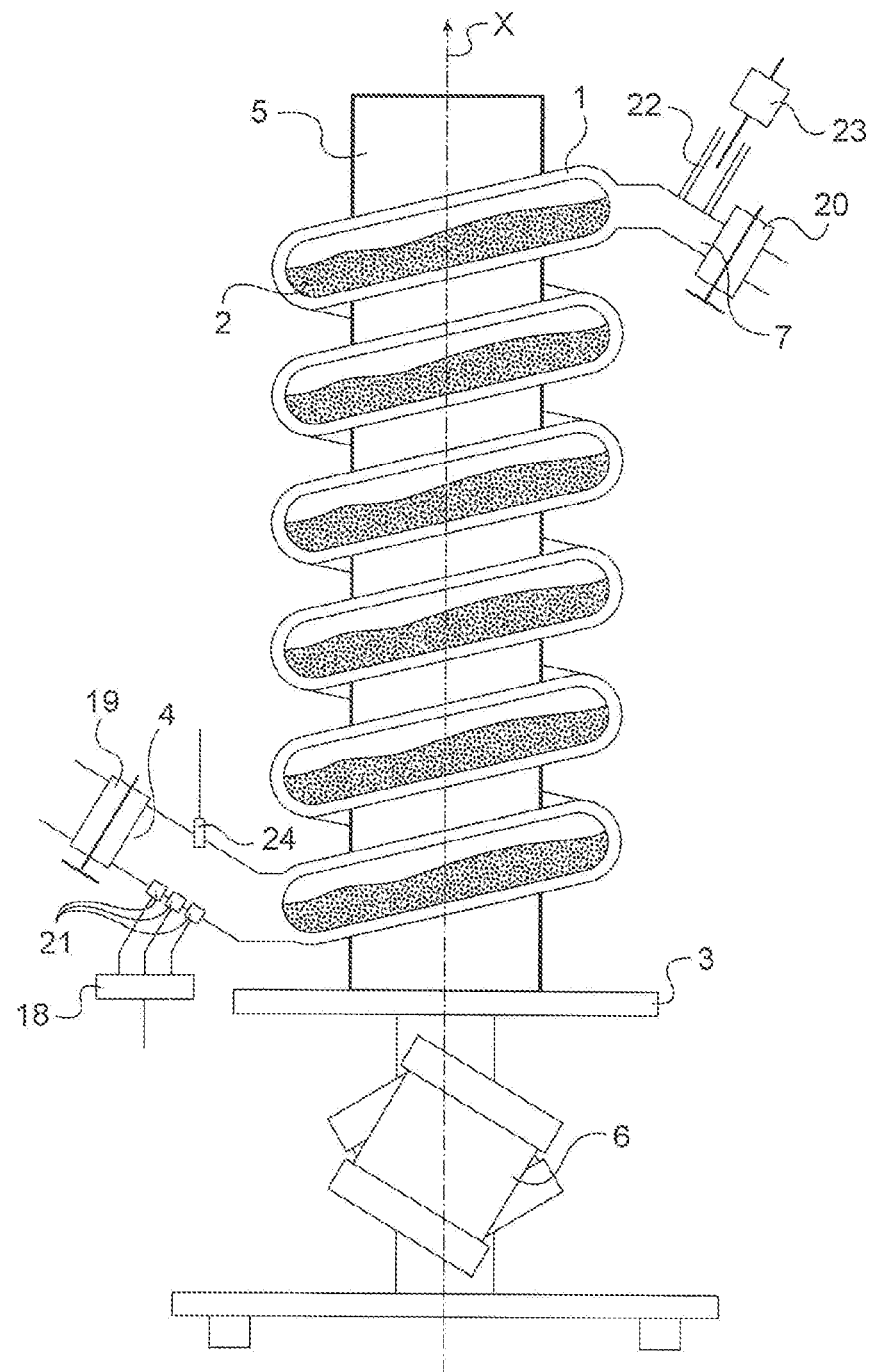

METHOD AND DEVICE FOR THE CONTINUOUS OZONE-BASED TREATMENT OF PARTICULATE PRODUCTS, COMPRISING MEANS FOR CONVEYING AND VIBRATING SAID PRODUCTS

The present invention relates to a method of treating substances in the form of divided solids. The divided substances are particularly, although not exclusively, food products such as spices, herbs, seasonings, dehydrated vegetables, dried fruits, powdered dairy products, or indeed aromatic or medicinal plants . . . .

TECHNOLOGICAL BACKGROUND

Because of its sterilizing properties, ozone is today currently used in the field of debacterizing food products.

Current ozone-based debacterization devices usually present an enclosure in which the substance to be treated is arranged before ozone is introduced therein. The substance is then left to rest for up to several hours in that ozonated atmosphere before the substance is removed.

However, it turns out that merely immersing grains in an ozonated atmosphere does not always lead to sufficient debacterization.

In order to improve debacterization, devices have been developed in which the substance is put into contact with the ozone on different occasions.

The "Oxygreen" (registered trademark) device is known and described in the book "Ozone in Food Processing" written by Colm O'Donnell, Brijesh K. Tiwari, P. J. Cullen, and Rip G. Rice and published by John Wiley & Sons. The "Oxygreen" device makes it possible to treat grains for use in the production of flours. The grains are placed in an enclosure having an ozone treatment zone in a bottom portion and a wormscrew for raising the substance to be treated from said bottom portion to the top portion of the enclosure: the substance thus flows naturally from the top portion to the bottom portion in order to reach the ozone treatment zone before being raised again by the wormscrew until it reaches the top portion where it flows once more towards the bottom portion. As it passes through the bottom portion of the enclosure, the substance is thus subjected to the action of the ozone in a manner that is discontinuous but repeated.

Although such a method procures better debacterization of the substance, it is nevertheless relatively difficult to implement, with there being a risk in particular of the substance being oxidized by the ozone.

OBJECT OF THE INVENTION

The present invention seeks to provide a method of treating a substance in the form of divided solids that mitigates the above-mentioned drawbacks at least in part. The present invention also seeks to provide a corresponding device for treating a substance in the form of divided solids.

GENERAL DEFINITION OF THE INVENTION

The above-mentioned problem is resolved in accordance with the invention by means of a method of continuously treating with ozone a substance in the form of divided solids, the method comprising the steps of:
  introducing the substance into the closed enclosure in which there exists an ozonated atmosphere under pressure;
  conveying the substance in the enclosure with continuous movement between an inlet of the enclosure and an outlet of the enclosure in such a manner that the substance is located continuously in the ozonated atmosphere while it is being conveyed in the enclosure, the substance being conveyed by vibration means causing the enclosure to vibrate; and
  unloading the substance from the enclosure via the outlet after a single passage of the substance through the enclosure.

Thus, unlike the above-mentioned prior art systems, which operate using ozone treatment that is discontinuous, and possibly repetitive, the method of the invention implements ozone treatment that is continuous: while the substance is being moved in the enclosure, the substance is simultaneously and continuously in contact with ozone. The entire enclosure thus forms the ozone treatment zone.

The substance is thus conveyed at the same time as it is subjected to the action of ozone in such a manner that one single passage of the substance is sufficient for proper treatment of the substance.

This makes it possible to better control treatment of the substance and in particular to better manage the action of ozone on the substance. It is thus possible to avoid the ozone oxidizing the substance, which would deteriorate the appearance, texture, smell, and taste of the substance.

In advantageous manner, the method of the invention makes it possible to limit the number of parameters that need to be set, in order both to treat the substance and also to avoid it being oxidized by the ozone, thereby making said method simpler to implement.

In addition, the method of the invention makes it possible to reduce the transit time of the substance through the enclosure. The inventors have thus been able to observe that the method of the invention makes it possible to have a substance transit time through the enclosure that lies in the range approximately ten minutes to one hour with an average substance transit time through the enclosure of about 20 minutes.

In particular manner, ozone is injected over a fraction only of the length of the enclosure.

In particular manner, ozone is injected into the enclosure a little downstream from the inlet of the enclosure.

In particular manner, the excess residual ozone present inside the enclosure is extracted via an outlet duct a little upstream from the outlet of the enclosure.

In particular manner, water is injected into the enclosure substantially at the inlet of the enclosure.

The invention also relates to a device for continuously treating a substance in the form of divided solids, the device comprising:
  a closed enclosure;
  injection means for injecting ozone into the enclosure and a purge circuit for purging excess ozone in the enclosure, the injection means and the purge circuit being shaped to generate an ozonated atmosphere under pressure; and
  conveyor means for conveying the substance with continuous movement between an inlet of the enclosure and an outlet of the enclosure in such a manner that the substance is located continuously in the ozonated atmosphere while it is being conveyed in the enclosure and is unloaded from the enclosure via the outlet after a single passage of the substance through the enclosure, said means comprising vibration means causing the enclosure to vibrate.

Other characteristics and advantages of the invention appear more clearly in the light of the following description and accompanying drawings, relating to a particular embodiment of the invention.

BRIEF DESCRIPTION OF THE DRAWINGS

Reference is made to the accompanying sole FIGURE, which is a diagram showing a longitudinal section view of a treatment device in a particular embodiment of the invention.

DETAILED DESCRIPTION OF A PARTICULAR EMBODIMENT OF THE INVENTION

With reference to the sole FIGURE, and in the particular embodiment of the invention, the treatment device comprises an enclosure 1 defining an inside space forming a treatment zone 2 for treating a substance in the form of divided solids. In this embodiment, the treatment device serves to debacterize the substance. Naturally, this application is not limiting and the treatment device could be used in order to decontaminate the substance, in particular to eliminate pesticide residues and mycotoxins.

The enclosure extends 1 longitudinally along an axis X. The enclosure 1 includes an inlet 4 at a first end and an outlet 7 at a second end. By way of example, the enclosure 1 is made of stainless steel. In this embodiment, the enclosure 1 is shaped into a coil wound around a central shaft 5 of the device while being fastened to said central shaft 5, the central shaft 5 also extending along the axis X.

The device further comprises means for vibrating the enclosure 1 so as to cause the substance to move from the inlet 4 of the enclosure 1 to the outlet 7 of the enclosure 1.

In known manner, the vibration means comprise a plate 3 on which are fastened both the central shaft 5 and unbalanced motors 6 arranged to cause said plate 3 and thus the central shaft 5 to vibrate together the enclosure 1.

By way of example, the vibration means are arranged in such a manner that the substance remains in the enclosure 1 for five minutes to one hour and preferably for five minutes to forty minutes. Alternatively, and by way of example, the vibration means are arranged in such a manner that the substance remains in the enclosure 1 for approximately ten minutes to one hour or preferably for approximately ten minutes to forty minutes.

The device includes means for injecting ozone into the enclosure 1, which means are connected in this embodiment to a source 18 for feeding ozone under pressure. The term "ozone" refers both to ozone generated from pure oxygen and to ozone generated from dried atmospheric air. By way of example, the ozone injection means are arranged in such a manner as to inject the ozone into the enclosure 1 at a concentration lying in the range 30 grams per cubic meter ($g/m^3$) to 90 $g/m^3$ and preferably at 60 $g/m^3$.

Since treatment in the enclosure 1 takes place under pressure and not at atmospheric pressure, the device and in particular the enclosure 1 are naturally shaped to withstand the pressure that exists inside the enclosure 1. In particular, the device includes a compression airlock 19 arranged upstream from the inlet 4 of the enclosure 1 and controlled by valves. In addition, the device includes a decompression airlock 20 arranged downstream from the outlet 7 and controlled by valves.

Specifically, the injection means comprise nozzles 21 (only some of which are visible in this embodiment) which are arranged in series. Preferably, the first nozzles 21 are arranged at the first end of the enclosure 1 a little downstream from the inlet 4, and the last nozzles 21 are arranged substantially at the first turn of the enclosure. This is found to facilitate controlling the action of ozone on the substance.

In a particular embodiment of the invention, the device comprises means (not shown in this embodiment) for controlling the nozzles 21, which means are arranged in such a manner that each nozzle 21 can be controlled individually. This further makes it possible to control even more effectively the action of ozone on the sub stance.

In addition the device includes a purge circuit for extracting excess ozone from the enclosure 1. In this embodiment, the purge circuit comprises an outlet duct 22 arranged at the second end of the enclosure 1 and a little upstream from the outlet 7 of the enclosure 1. The purge circuit further comprises a residual ozone destroyer 23 (such as a burner or a catalytic destroyer) connected to the outlet duct 22 in order to destroy the excess residual ozone extracted from the enclosure 1.

The arrangement of the nozzles 21 and of the outlet duct 22 as described herein enables the ozone to flow in the enclosure 1 in the same direction as the flow of substance in the enclosure 1. This is found to facilitate controlling the action of ozone on the substance.

In this embodiment, the injection means and the purge circuit are arranged to generate an ozonated atmosphere inside the enclosure 1 such that the mass of ozone present inside the enclosure 1 lies in the range 2 grams (g) to 18 g per kilogram of substance present in the enclosure 1. Preferably, the injection means and the purge circuit are arranged to generate an ozonated atmosphere inside the enclosure 1 such that the mass of ozone present inside the enclosure 1 lies in the range 2 g to 10 g per kilogram of substance present in the enclosure 1 and more preferably in the range 3 g to 5 g per kilogram of substance present in the enclosure 1. Alternatively, the injection means and the purge circuit are arranged to generate an ozonated atmosphere inside the enclosure 1 such that the mass of ozone present inside the enclosure 1 is substantially 10 g per kilogram of substance present in the enclosure 1.

Furthermore, in this embodiment the injection means and the purge circuit are shaped to generate an ozonated atmosphere inside the enclosure 1 presenting a pressure lying in the range 0.1 bar to 1 bar. Preferably, the injection means and the purge circuit are arranged to generate an ozonated atmosphere inside the enclosure 1 of 0.6 bar.

In addition, the device comprises means for humidifying the ozonated atmosphere and consequently humidifying substance. In this embodiment, said means comprise a water injector 24 that is arranged at the first end 3 of the enclosure 1 a little downstream from the inlet 4 of the enclosure 1. In this embodiment, the water injector 24 is arranged to be located directly above some of the ozone injection nozzles 21. This enables the substance to be relatively well humidified on entering the ozonated atmosphere.

Additionally or as a replacement, depending on the hygroscopicity of the substance, the device may include means for homogeneously pre-humidifying the substance, which means are arranged upstream from the inlet 4 of the device.

Thus, in order to treat the substance, the substance is introduced into the enclosure 1 via the inlet 4. The substance is then humidified by the water injector 24 and is in contact with the ozone present inside the enclosure 1. The substance is thus conveyed into the enclosure 1 by the means for vibrating the enclosure 1 before being unloaded via the outlet 7.

It should be observed that during its single passage through the enclosure 1, the conveyed substance is constantly moving and subjected to the ozonated atmosphere, which enhances the treatment.

This provides a method of debacterizing a substance by using ozone.

In addition, the invention advantageously makes it possible to limit the number of parameters that serve to control treatment of the substance. The parameters that it is possible to adjust in order to optimize treatment are as follows:
- the transit time of the substance in the enclosure 1 (acting on the intensity of the vibration emitted by the vibration means of the enclosure 1);
- the moisture content (acting on the humidifying means); and
- the mass percentage of ozone relative to the mass of substance (by acting on the ozone injection means and the purge circuit).

Associating for the first time the principle of continuously conveying the substance with simultaneous exposure to ozone provides multiple advantages, and in particular better control of the treatment of the substance and also treatment that is faster.

The invention thus paves the way to treating particularly delicate substances, such as spices (pepper, curry, turmeric, etc. . . . ), herbs, seasonings, dehydrated vegetables, aromatic or medicinal plants, dried fruits, powdered dairy products . . . .

The invention is not limited to the implementation described but, on the contrary, encompasses any variant coming within the ambit of the invention.

The nozzles could be arranged differently to the arrangement described. By way of example, the nozzles could be arranged so as to be present along the entire length of the enclosure. The nozzles could also be present at the outlet of the enclosure only and the purge circuit could be arranged at the inlet of the enclosure so that the ozone flows as a counter-flow to the flow of substance inside the enclosure.

In addition, the means for humidifying the substance may be different from those described. By way of example, said means could be arranged upstream from the inlet of the enclosure, e.g. before the compression airlock. Additionally or as a replacement, the humidifying means may comprise a misting circuit arranged over all or part of the length of the enclosure in order to better control the moisture content of the ozonated atmosphere that exists inside the enclosure and therefore the moisture content of the substance.

The means for humidifying the substance may spray ozonated water instead of water as described in order to contribute, in co-operation with the ozone injection means, to creating an ozonated atmosphere inside the enclosure. Furthermore, although as described herein the substance humidifying means are separate from the ozone injection means, they could be combined, the injection means thus directly spraying ozonated water into the enclosure in order to create an ozonated atmosphere therein.

The device could also include drying means arranged for example at the outlet of the enclosure in order to better control the moisture content of the ozonated atmosphere that exists inside the enclosure and therefore the moisture content of the sub stance.

The invention claimed is:

1. A method of continuously treating a substance in the form of divided solids, the method comprising:
   introducing the substance into a closed enclosure in which there exists an ozonated atmosphere under pressure;
   conveying the substance in the enclosure with continuous movement between an inlet of the enclosure and an outlet of the enclosure in such a manner that the substance is located continuously in the ozonated atmosphere under pressure while it is being conveyed in the enclosure, the substance being conveyed by vibration means causing the enclosure to vibrate; and
   unloading the substance from the enclosure via the outlet after a single passage of the substance through the enclosure.

2. The method according to claim 1, wherein ozone is injected over a fraction only of the length of the enclosure.

3. The method according to claim 1, wherein ozone is injected into the enclosure a little downstream from the inlet of the enclosure.

4. The method according to claim 1, wherein excess residual ozone present inside the enclosure is extracted via an outlet duct a little upstream from the outlet of the enclosure.

5. The method according to claim 1, wherein water is injected into the enclosure substantially at the inlet of the enclosure.

6. A device for continuously treating a substance in the form of divided solids, the device comprising:
   a closed enclosure;
   injection means for injecting ozone into the enclosure and a purge circuit for purging excess ozone in the enclosure, the injection means and the purge circuit being shaped to generate an ozonated atmosphere under pressure; and
   conveyor means for conveying the substance with continuous movement between an inlet of the enclosure and an outlet of the enclosure in such a manner that the substance is located continuously in the ozonated atmosphere under pressure while it is being conveyed in the enclosure and is unloaded from the enclosure via the outlet after a single passage of the substance through the enclosure, said means comprising vibration means causing the enclosure to vibrate.

7. A device for continuously treating a substance in the form of divided solids, the device comprising:
   a closed enclosure being shaped into a coil wound around a central shaft;
   injection means for injecting ozone into the enclosure and a purge circuit for purging excess ozone in the enclosure, the injection means and the purge circuit being shaped to generate an ozonated atmosphere under pressure; and
   conveyor means for conveying the substance with continuous movement between an inlet of the enclosure and an outlet of the enclosure in such a manner that the substance is located continuously in the ozonated atmosphere under pressure while it is being conveyed in the enclosure and is unloaded from the enclosure via the outlet after a single passage of the substance through the enclosure, said means comprising vibration means causing the enclosure to vibrate.

8. A device for continuously treating a substance in the form of divided solids, the device comprising:
   a closed enclosure;
   injection means for injecting ozone into the enclosure and a purge circuit for purging excess ozone in the enclosure, the injection means and the purge circuit being shaped to generate an ozonated atmosphere under pressure; and
   conveyor means for conveying the substance with continuous vertical movement between a bottom inlet of the enclosure and an upper outlet of the enclosure in such a manner that the substance is located continuously in the ozonated atmosphere under pressure while it is being conveyed in the enclosure and is unloaded from the enclosure via the outlet after a single passage of the substance through the enclosure, said means comprising vibration means causing the enclosure to vibrate.

9. A method of continuously treating a substance in the form of divided solids, the method comprising:

introducing the substance into a closed enclosure in which there exists an ozonated atmosphere under pressure;

conveying the substance in the enclosure with continuous movement between an inlet of the enclosure and an outlet of the enclosure in such a manner that the substance is located continuously in the ozonated atmosphere under pressure so that the treatment of the substance takes place under pressure, the substance being conveyed by vibration means causing the enclosure to vibrate; and unloading the substance from the enclosure via the outlet after a single passage of the substance through the enclosure.

10. A device for continuously treating a substance in the form of divided solids, the device comprising:

a closed enclosure;

injection means for injecting ozone into the enclosure and a purge circuit for purging excess ozone in the enclosure, the injection means and the purge circuit being shaped to generate an ozonated atmosphere under pressure; and conveyor means for conveying the substance with continuous movement between an inlet of the enclosure and an outlet of the enclosure in such a manner that the substance is located continuously in the ozonated atmosphere under pressure so that the treatment of the substance takes place under pressure while it is being conveyed in the enclosure and is unloaded from the enclosure via the outlet after a single passage of the substance through the enclosure, said means comprising vibration means causing the enclosure to vibrate.

* * * * *